United States Patent
Calabrese et al.

(10) Patent No.: US 12,402,780 B2
(45) Date of Patent: Sep. 2, 2025

(54) DEVICE TIP (71) Applicant: Boston Scientific Scimed, Inc., Maple Grove, MN (US)

(72) Inventors: Andrew Calabrese, Lancaster, MA (US); Mark D. Wood, Sterling, MA (US); Gregory Thomas Hughes, Hanson, MA (US); Brian Gaffney, Rutland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/364,533

(22) Filed: Aug. 3, 2023

(65) Prior Publication Data

US 2023/0371790 A1    Nov. 23, 2023

Related U.S. Application Data

(63) Continuation of application No. 17/724,284, filed on Apr. 19, 2022, now Pat. No. 11,751,751, which is a
(Continued)

(51) Int. Cl.
*A61B 1/00* (2006.01)
*A61B 1/005* (2006.01)
(Continued)

(52) U.S. Cl.
CPC ........ *A61B 1/00098* (2013.01); *A61B 1/0011* (2013.01); *A61B 1/00174* (2013.01);
(Continued)

(58) Field of Classification Search
CPC ... A61B 1/00098; A61B 1/018; A61B 1/0008; A61B 1/0057
See application file for complete search history.

(56) References Cited

U.S. PATENT DOCUMENTS 1,901,731 A   *   3/1933   Buerger ............. A61B 1/00135
                                                               600/107
3,561,432 A      2/1971   Yamaki et al.
(Continued)

FOREIGN PATENT DOCUMENTS

JP        S56-073802 U    6/1981
JP        S57-188231      11/1982
(Continued)

OTHER PUBLICATIONS

Japanese Office Action issued on Feb. 1, 2022 in counterpart Japanese Patent Application No. 2019-547150 (5 pages, in Japanese).
(Continued)

*Primary Examiner* — Alexandra L Newton
(74) *Attorney, Agent, or Firm* — Bookoff McAndrews, PLLC (57) ABSTRACT

In one aspect of the present disclosure, a device may include a shaft having a distal end, and a tip at the distal end of the shaft. The tip may include an opening defined by a surface of the tip. An instrument inserted through the shaft may extend distally out of the opening. The device also may include an elevator for engaging the instrument. The elevator may include a proximal end fixed relative to the surface of the tip, a proximal portion extending distally from the proximal end, and a distal portion extending distally from the proximal portion. A force exerted on the elevator bends the proximal portion to deflect the distal portion without bending of the distal portion.

20 Claims, 4 Drawing Sheets

Related U.S. Application Data continuation of application No. 15/909,205, filed on Mar. 1, 2018, now Pat. No. 11,330,965.

(60) Provisional application No. 62/466,657, filed on Mar. 3, 2017.

(51) Int. Cl.
*A61B 1/015* (2006.01)
*A61B 1/018* (2006.01)
*A61B 1/12* (2006.01)

(52) U.S. Cl.
CPC .............. *A61B 1/015* (2013.01); *A61B 1/018* (2013.01); *A61B 1/0052* (2013.01); *A61B 1/126* (2013.01)

(56) References Cited

U.S. PATENT DOCUMENTS

| | | |
|---|---|---|
| 3,871,365 A | 3/1975 | Chikama |
| 3,888,237 A | 6/1975 | Mori |
| 3,915,157 A | 10/1975 | Mitsui |
| 4,190,041 A | 2/1980 | Chikama |
| 4,407,273 A | 10/1983 | Ouchi |
| 4,436,087 A | 3/1984 | Ouchi |
| 4,452,236 A | 6/1984 | Utsugi |
| 4,474,174 A | 10/1984 | Petruzzi |
| 4,589,403 A | 5/1986 | Ouchi et al. |
| 4,593,680 A | 6/1986 | Kubokawa |
| 4,697,576 A | 10/1987 | Krauter |
| 4,706,655 A | 11/1987 | Krauter |
| 4,868,644 A | 9/1989 | Yabe et al. |
| 4,949,706 A | 8/1990 | Thon |
| 5,325,847 A | 7/1994 | Matsuno |
| 5,460,168 A * | 10/1995 | Masubuchi ........ A61B 1/00098 600/107 |
| 5,562,600 A | 10/1996 | Matsuno |
| 5,569,157 A * | 10/1996 | Nakazawa ......... A61B 1/00098 600/106 |
| 5,569,162 A | 10/1996 | Komi |
| 5,860,913 A | 1/1999 | Yamaya et al. |
| 5,865,726 A | 2/1999 | Katsurada et al. |
| 5,868,663 A | 2/1999 | Katsurada et al. |
| 6,238,336 B1 | 5/2001 | Ouchi |
| 6,338,717 B1 | 1/2002 | Ouchi |
| 6,582,357 B2 | 6/2003 | Ouchi et al. |
| 6,699,183 B1 | 3/2004 | Wimmer |
| 6,916,286 B2 | 7/2005 | Kazakevich |
| 7,341,555 B2 | 3/2008 | Ootawara et al. |
| 7,691,055 B2 | 4/2010 | Carter et al. |
| 7,753,843 B2 | 7/2010 | Wood et al. |
| 7,794,389 B2 | 9/2010 | Carter |
| 7,815,564 B2 | 10/2010 | Geitz et al. |
| 8,066,631 B2 | 11/2011 | Wimmer |
| 8,109,872 B2 | 2/2012 | Kennedy, II et al. |
| 8,372,000 B2 | 2/2013 | Weisman |
| 8,435,170 B2 | 5/2013 | Wood et al. |
| 8,475,360 B2 | 7/2013 | Brown |
| 8,690,756 B2 | 4/2014 | Deal |
| 8,696,550 B2 | 4/2014 | Surti |
| 8,753,263 B2 | 6/2014 | Arai |
| 8,795,156 B2 | 8/2014 | Geitz et al. |
| 8,870,754 B2 | 10/2014 | Wood et al. |
| 8,870,758 B2 | 10/2014 | Dahmen et al. |
| 8,888,681 B2 | 11/2014 | Weisman |
| 8,926,499 B2 | 1/2015 | Shaw |
| 8,945,153 B2 | 2/2015 | Surti |
| 9,149,173 B2 | 10/2015 | Scopton et al. |
| 9,179,825 B2 | 11/2015 | Geitz et al. |
| 9,427,139 B2 | 8/2016 | Tinkham et al. |
| 9,445,794 B2 | 9/2016 | Shaw |
| 9,668,643 B2 | 6/2017 | Kennedy, II et al. |
| 9,693,803 B2 | 7/2017 | Mamiya |
| 9,877,638 B2 | 1/2018 | Buerk |
| 9,880,380 B2 | 1/2018 | Daidoji et al. |
| 2002/0087100 A1 | 7/2002 | Onuki et al. |
| 2005/0131278 A1 | 6/2005 | Dickopp |
| 2006/0138309 A1 | 6/2006 | Wimmer |
| 2007/0197871 A1 | 8/2007 | Geitz et al. |
| 2007/0208220 A1 | 9/2007 | Carter |
| 2007/0265494 A1 | 11/2007 | Leanna et al. |
| 2008/0188862 A1 | 8/2008 | Saitou |
| 2008/0214890 A1 | 9/2008 | Motai et al. |
| 2008/0287961 A1 | 11/2008 | Miyamoto et al. |
| 2009/0062615 A1 | 3/2009 | Yamaya |
| 2010/0228086 A1 | 9/2010 | Ohki et al. |
| 2010/0256446 A1 | 10/2010 | Raju |
| 2011/0152610 A1 | 6/2011 | Trusty et al. |
| 2011/0152618 A1 | 6/2011 | Surti |
| 2013/0331696 A1 | 12/2013 | Morimoto |
| 2015/0031948 A1 | 1/2015 | Wood et al. |
| 2015/0157189 A1 | 6/2015 | Shimada |
| 2016/0227988 A1 | 8/2016 | Jiang et al. |
| 2016/0367233 A1 | 12/2016 | Mamiya et al. |
| 2017/0014116 A1 | 1/2017 | Nakazato |
| 2017/0020548 A1 | 1/2017 | Levasseur et al. |
| 2017/0325666 A1 | 11/2017 | Jiang et al. |
| 2019/0246886 A1* | 8/2019 | Harada .................. A61B 1/018 |

FOREIGN PATENT DOCUMENTS

| | | |
|---|---|---|
| JP | S60-220031 | 11/1985 |
| JP | S62-142310 U | 9/1987 |
| JP | H02 82304 U | 6/1990 |
| JP | H6-315458 | 11/1994 |
| JP | H06-319678 | 11/1994 |
| JP | H0723900 A | 1/1995 |
| JP | H07-23900 | 3/1995 |
| JP | H8-243076 | 9/1996 |
| JP | 2000116598 A | 4/2000 |
| JP | 2002017655 A | 1/2002 |
| JP | 2003305001 A | 10/2003 |
| JP | 3725849 B2 | 12/2005 |
| JP | 3772107 B2 | 5/2006 |
| JP | 3956212 B2 | 8/2007 |
| JP | 4009621 B2 | 11/2007 |
| JP | 4014707 B2 | 11/2007 |
| JP | 4025755 B2 | 12/2007 |
| JP | 4160577 B2 | 10/2008 |
| JP | 4163438 B2 | 10/2008 |
| JP | 4201408 B2 | 12/2008 |
| JP | 2010004945 A | 1/2010 |
| JP | 4414827 B2 | 2/2010 |
| JP | 4657054 B2 | 3/2011 |
| JP | 4716594 B2 | 7/2011 |
| JP | 4789487 B2 | 10/2011 |
| JP | 4875774 B2 | 2/2012 |
| JP | 5011024 B2 | 8/2012 |
| JP | 5078279 B2 | 11/2012 |
| JP | 5313068 B2 | 10/2013 |
| JP | 5393383 B2 | 1/2014 |
| JP | 5430299 B2 | 2/2014 |
| JP | 5855628 B2 | 2/2016 |
| JP | 2016131578 A | 7/2016 |
| JP | 5970144 B1 | 8/2016 |
| JP | 2016174818 A | 10/2016 |
| JP | 2016174819 A | 10/2016 |
| JP | 6110828 B2 | 4/2017 |
| JP | 6110829 B2 | 4/2017 |
| JP | 6138404 B2 | 5/2017 |
| JP | 2017079876 A | 5/2017 |
| JP | 2017079877 A | 5/2017 |
| JP | 6148219 B2 | 6/2017 |
| JP | 6157791 B2 | 7/2017 |
| JP | 6173287 B2 | 8/2017 |
| JP | 2017136298 A | 8/2017 |
| JP | 2017148096 A | 8/2017 |
| JP | 6218642 B2 | 10/2017 |
| JP | 6249978 B2 | 12/2017 |
| JP | 2017213061 A | 12/2017 |
| JP | 6263494 B2 | 1/2018 |
| JP | 6266557 B2 | 1/2018 |
| JP | 6271465 B2 | 1/2018 |

(56) References Cited

FOREIGN PATENT DOCUMENTS

| KR | 10-2007-0031346 A | 3/2007 |
|----|-------------------|--------|
| WO | WO 2013099390 A1 | 7/2013 |
| WO | WO 2015182540 A1 | 12/2015 |
| WO | WO 2017038471 A1 | 3/2017 |
| WO | WO 2017179293 A1 | 10/2017 |

OTHER PUBLICATIONS

European Office Action issued on May 30, 2022 in European Patent Application No. 18711753.6 (7 pages, in English).
Japan Patent Office (Jpo), Japanese Patent Application No. 2024-030711, Office Action dated Dec. 17, 2024.

\* cited by examiner

DEVICE TIP

CROSS-REFERENCE TO RELATED APPLICATION(S)

This patent application is a continuation of and claims the benefit of priority to U.S. Nonprovsional patent application Ser. No. 17/724,284, filed on Apr. 19, 2022, which is a continuation of U.S. Nonprovisional patent application Ser. No. 15/909,205, filed on Mar. 1, 2018, which claims the benefit under 35 U.S.C. § 119 to U.S. Provisional Application No. 62/466,657, filed on Mar. 3, 2017, each of which is incorporated herein by reference in its entirety.

TECHNICAL FIELD

Various aspects of the present disclosure relate generally to tips for devices. More specifically, the present disclosure relates to endoscope tips for positioning endoscopic instruments.

BACKGROUND

Endoscopic retrograde cholangiopancreatography (ERCP) is a technique to treat patients with pancreaticobiliary disorders. In some instances, ERCP is performed using a side viewing endoscope. A tip of the side viewing endoscope may include side viewing optics, an optics lens wash, a side viewing light source, a side exit working channel, and an elevator assembly for elevating an instrument extending out of the side exit working channel. These features may aid a user in cannulating a subject's papilla, and accessing a target site in the subject's pancreas, with instruments for diagnostic and/or therapeutic procedures. However, elevator assemblies may have complex designs with a multitude of components, making them expensive to manufacture and maintain (e.g., clean and/or repair). Reducing the complexity of an elevator assembly may reduce overall costs associated with using an endoscope. Moreover, when overall costs fall to a certain threshold, it may be practical for the endoscope to be used as a single-use endoscope. By using the endoscope only once before discarding it, cost and time burdens associated with maintaining the endoscope may be eliminated, and the risk of exposing a subject to infection through inadequate cleaning of the endoscope also may be eliminated, leading to improved outcomes.

SUMMARY

Aspects of the present disclosure relate to, among other things, tips for devices. Each of the aspects disclosed herein may include one or more of the features described in connection with any of the other disclosed aspects.

In one aspect of the present disclosure, a device may include a shaft having a distal end, and a tip at the distal end of the shaft. The tip may include an opening defined by a surface of the tip. An instrument inserted through the shaft may extend distally out of the opening. The device also may include an elevator for engaging the instrument. The elevator may include a proximal end fixed relative to the surface of the tip, a proximal portion extending distally from the proximal end, and a distal portion extending distally from the proximal portion. A force exerted on the elevator bends the proximal portion to deflect the distal portion without bending of the distal portion.

According to another aspect of the present disclosure, the device may include one or more of the features below. The distal portion may have a greater cross-sectional area than the proximal portion. The distal portion may be thicker than the proximal portion along an anterior-posterior direction, the anterior-posterior direction being perpendicular to a proximal-distal direction. The tip may be comprised of a single material. The elevator may be comprised of a single material. An outer surface of the elevator and the surface of the tip may be portions of a continuous surface. An outer surface of the distal portion of the elevator may be continuous with the outer surface of the proximal portion of the elevator. The proximal portion may have a substantially straight rest configuration and a bent configuration. The proximal portion may move the distal portion through an arcuate path in an anterior direction and a proximal direction as the proximal portion moves from the rest configuration to the bent configuration.

In another aspect of the present disclosure, a device may include a shaft having a distal end. The device also may include a tip at the distal end of the shaft. The tip may include an instrument opening. An instrument inserted through the shaft may extend distally out of the instrument opening. The tip also may include an elevator for engaging the instrument as the instrument extends distally out of the instrument opening. The elevator may include a passage extending therethrough. The device also may include a control wire coupled to the elevator. A proximal pulling force exerted on the control wire may deflect the elevator. The device also may include a first control wire opening and a second control wire opening. A first portion of the control wire may extend from the first control wire opening to the passage. A second portion of the control wire may extend from the second control wire opening to the passage. A third portion of the control wire may extend through the passage to link the first portion of the control wire to the second portion of the control wire.

According to another aspect of the present disclosure, the device may include one or more of the features below. A handle at a proximal end of the shaft. The handle may include an actuation mechanism for exerting the proximal pulling force on the control wire. The actuation mechanism may be operatively coupled to the first portion of the control wire and the second portion of the control wire to exert the proximal pulling force simultaneously on the first portion of the control wire and the second portion of the control wire. The elevator may include opposing side surfaces. At least one of the side surfaces may include a channel for receiving at least a portion of the control wire. An opening into the passage may be in the channel. The tip may include sidewalls on opposing sides of the elevator. At least one of the sidewalls may include a channel for receiving at least a portion of the control wire. The tip may be a one-piece, monolithic, polymer component.

In another aspect of the present disclosure, a device may include a shaft having a distal end. The device also may include a tip at the distal end of the shaft. The tip may include an elevator. An instrument inserted through the shaft may extend distally to engage the elevator. The device also may include an actuator to deflect the elevator. The elevator may include a proximal portion having a proximal end fixed relative to the shaft. The elevator also may include a distal portion extending distally from the proximal portion. The proximal portion may have a smaller cross-sectional area than the distal portion, such that a force exerted on the elevator may bend the proximal portion to deflect the distal portion. The elevator may be made of a single, continuous piece of material.

According to another aspect of the present disclosure, the device may include one or more of the features below. The single, continuous piece of material may be a single, continuous piece of injection-molded polymer. The proximal portion may include one or more indentations, such that the proximal portion may have one or more thin regions and one or more thick regions, to facilitate bending of the proximal portion along the one or more thin regions. The tip may further include at least one portion coupled to the single, continuous piece of material. The at least one portion may be made of a more rigid material than the single, continuous piece of material. The actuator may include a control wire coupled to the elevator.

It may be understood that both the foregoing general description and the following detailed description are exemplary and explanatory only and are not restrictive of any claimed inventions.

BRIEF DESCRIPTION OF THE DRAWINGS

The accompanying drawings, which are incorporated in and constitute a part of this specification, illustrate aspects of the present disclosure and together with the description, serve to explain the principles of the disclosure.

DETAILED DESCRIPTION

The present disclosure is drawn generally to tips for devices, and more specifically to endoscope tips for positioning endoscopic instruments. Reference now will be made in detail to aspects of the present disclosure, examples of which are illustrated in the accompanying drawings. Wherever possible, the same reference numbers will be used throughout the drawings to refer to the same or like parts. The term "distal" refers to a portion farthest away from a user when introducing an instrument into a subject. By contrast, the term "proximal" refers to a portion closest to the user when placing the instrument into the subject. The terms "anterior" and "posterior" refer to directions and/or regions extending perpendicular to proximal and distal directions. Though the following description refers to "endoscope" or "endoscopy," the principles/aspects described herein may be used with any suitable introduction sheath or device, even if such sheath or device fails to include one or more features typically associated with "endoscopes." It may be understood that both the foregoing general description and the following detailed description are exemplary and explanatory only and are not restrictive of the features claimed. Further, as used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal."

Figure 1:
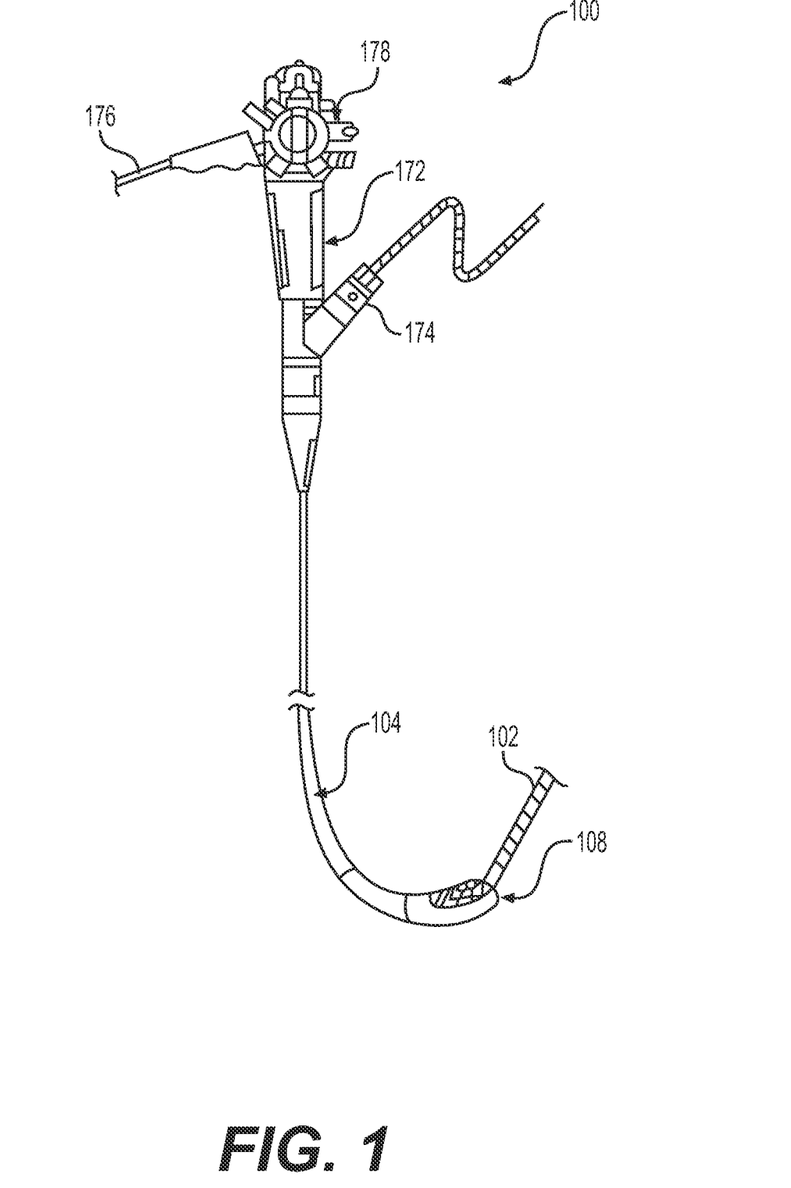
FIG. 1 shows an endoscope, in accordance with aspects of the present disclosure.

FIG. 1 shows a device 100 for positioning an instrument 102. Device 100 may be any type of endoscope, such as a duodenoscope. Instrument 102 may include, for example, a guidewire, cutting or grasping forceps, a biopsy device, a snare loop, an injection needle, a cutting blade, scissors, a retractable basket, a retrieval device, an ablation and/or electrophysiology catheter, a stent placement device, a surgical stapling device, a balloon catheter, a laser-emitting device, and/or any other suitable instrument. In one example, device 100 may to facilitate cannulation of a subject's papilla, and placement of instrument 102 therein, during an ERCP procedure.

Device 100 may include a shaft 104. Shaft 104 may include a tube 106 that may be sufficiently flexible so as to have the ability to bend, rotate, and/or twist while being inserted into and/or through a subject's tortuous anatomy to a target site in the subject's body. Shaft 104 may have one or more lumens (not shown) extending therethrough. The lumens may include, for example, control wire lumens for receiving one or more control wires, a working lumen for receiving instrument 102, a fluid lumen for delivering a fluid, an illumination lumen for receiving at least a portion of an illumination assembly (not shown), and/or an imaging lumen for receiving at least a portion of an imaging assembly (not shown).

Device 100 also may include a tip 108 at a distal end of shaft 104. Tip 108 may be attached to the distal end of shaft 104. For example, tip 108 may be a cap configured to receive the distal end of shaft 104. Tip 108 may include one or more openings that communication with the lumens of shaft 104. For example, tip 108 may include control wire openings 110 and 112 through which one or more control wires may exit from the control wire lumens of shaft 104, a working opening 114 through which instrument 102 may exit from the working lumen of shaft 104, a fluid opening or nozzle 116 through which fluid may be emitted from the fluid lumen of shaft 104, an illumination opening or window 118 through which light may be emitted, and/or an imaging opening or window 120 for receiving light used by the imaging device to generate an image. While not depicted in FIG. 1, it should be understood that illumination opening 118 may include a light emitter (e.g., a light-emitting diode, or the like) coupled to a cable or wire running through the illumination lumen of shaft 104, and/or imaging opening 120 may include an imager (e.g., a charge-coupled device image sensor, a complementary metal-oxide image semiconductor, or the like) coupled to a cable or wire running through the imaging lumen of shaft 104.

Control wire openings 110 and 112 may be on a distal-facing surface 124 of tip 108. Working opening 114 may be on a distal-facing surface 126 of tip 108. Distal-facing surface 126 may be recessed from distal-facing surface 124 in a proximal direction. Illumination opening 118 and imaging opening 120 may be on an anterior-facing surface 128.

Fluid opening 116 may be on distal-facing surface 124, and may open toward illumination opening 118 and imaging opening 120 to, for example, direct a stream of rinsing fluid across illumination opening 118 and/or imaging opening 120 to wash off bodily fluids or debris.

Figure 2:
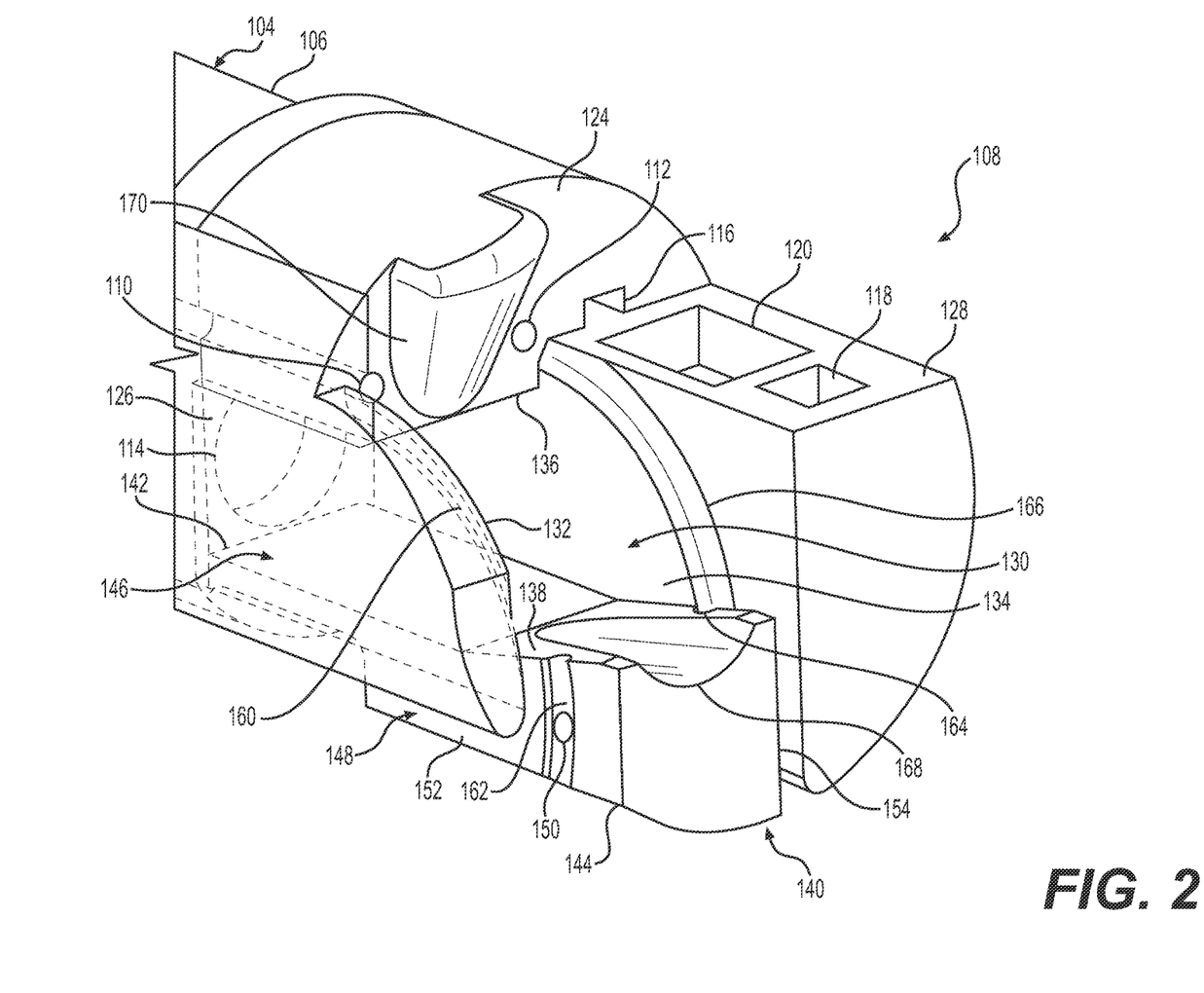
FIG. 2 shows a perspective view of a tip of the endoscope of FIG. 1, in accordance with aspects of the present disclosure.

Working opening 114 may open into a cavity 130 of tip 108. Cavity 130 may be defined by distal-facing surface 126, lateral-facing sidewalls 132 and 134, a posterior-facing surface 136, and an anterior-facing surface 138 of an elevator 140. Instrument 102 may extend distally out of working opening 114 and into cavity 130, where instrument 102 may be positioned for engagement with anterior-facing surface 138 of elevator 140. Anterior-facing surface 138 of elevator 140 may include, for example, an indentation 168 (e.g., a slot, groove, cavity, or the like) formed therein. Indentation 168 may receive at least a portion of instrument 102 to exert a holding or gripping force on instrument 102.

Elevator 140 may be cantilevered, having a fixed proximal end 142 at distal-facing surface 126, and a free distal end 144. Elevator 140 may include a proximal portion 146 and a distal portion 148. Proximal portion 146 may be thinner than distal portion 148 to facilitate bending of proximal portion 146. This is because distal portion 148, due to its thickness, may be more rigid than proximal portion 146. In some examples, proximal portion 146 may bend while distal portion 148 may remain unbent.

Proximal portion 146 may have a rectangular cross-sectional shape to facilitate bending along the anterior-posterior direction. Additionally or alternatively, a length of proximal portion 146 (along the proximal-distal direction) may be greater than a width of proximal portion 146 (along a lateral direction perpendicular to the proximal-distal direction), and the width of proximal portion 146 may be greater than a height/thickness of proximal portion 146 (along the anterior-posterior direction). Additionally or alternatively, proximal portion 146 may have a substantially constant thickness all the way from distal-facing surface 126 to a proximal end of distal portion 148, where elevator 140 may undergo an abrupt increase in thickness. Anterior-facing surface 138 may be angled (e.g., inclined) relative to proximal portion 146 to facilitate engagement between anterior-facing surface 138 and instrument 102. Additionally or alternatively, one or more of a posterior-facing surface of proximal portion 146 and an anterior-facing surface of proximal portion 146 may be substantially planar and/or substantially perpendicular to one or more of lateral-facing sidewalls 132 and 134.

Proximal portion 146 may act as a living hinge to allow distal portion 148 of elevator 140 to move relative to the rest of tip 108. Proximal portion 146 may bend such that distal portion 148 may travel along an arcuate path that may cover a distance in a proximal-distal direction and an anterior-posterior direction. In some examples, elevator 140 may be integral with the rest of tip 108. For example, tip 108, as shown in FIG. 2, may be a single, monolithic, injection-molded component. Tip 108 may be made of a polymeric material, such as polyethylene, polypropylene, and/or any other suitable polymer. Tip 108 may be made by any other suitable process, and with any other suitable material, for forming tip 108 as a single piece of the same material throughout.

Distal portion 148 may be thicker than proximal portion 146 to provide space for a passage 150. The thickness of distal portion 148 may ensure that distal portion 148 does not bend, and that bending of elevator 140 is limited to proximal portion 146. Passage 150 may be a through-hole extending between opposing lateral-facing surfaces 152 and 154 of elevator 140. Passage 150 may receive control wire 122. For example, a first portion 156 of control wire 122 may extend distally from control wire opening 110 to lateral-facing surface 152 and passage 150 (see FIG. 3). A second portion 158 of control wire 122 may extend distally from control wire opening 112 to lateral-facing surface 154 and passage 150. A third portion (not shown) of control wire 122 may extend through passage 150. First portion 156, second portion 158, and the third portion of control wire 122 may form a U-shaped extent of control wire 122.

Figure 3:
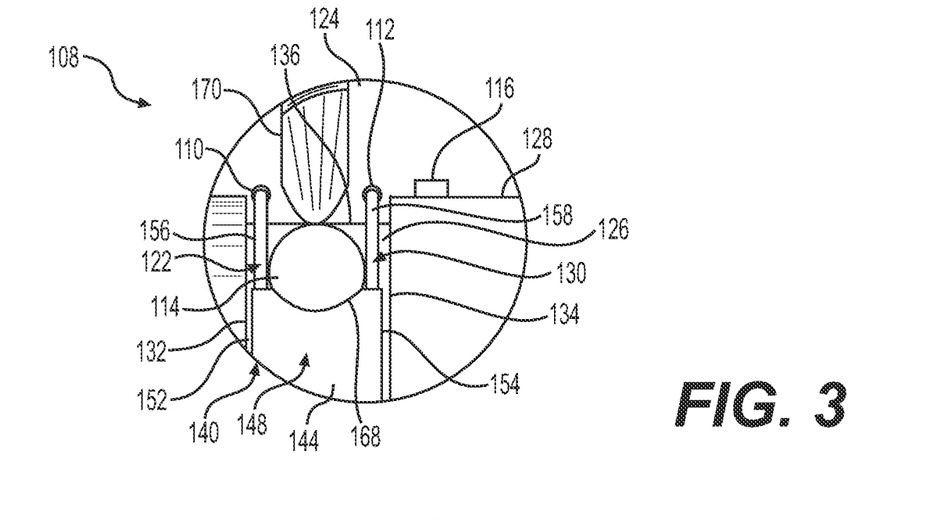
FIG. 3 shows a front view of the tip of the endoscope of FIG. 1, in accordance with aspects of the present disclosure.

Channels 160, 162, 164, and 166 may be provided in sidewall 132, lateral-facing surface 152, lateral-facing surface 154, and sidewall 134 for receiving portions of control wire 122. The received portions of control wire 122 may slide along channels 160 and 166 as control wire 122 is retracted into and/or extended out of control wire openings 110 and 112. In the depicted example, passage 150 may open into channels 162 and 164. Control wire 122 may be strung through passage 150 by deflecting elevator 140 in a posterior direction to expose passage 150 from behind sidewalls 132 and 134, inserting control wire 122 through passage 150, aligning control wire 122 with channels 160, 162, 164, and 166, inserting control wire 122 into control wire openings 110 and 112.

Figure 4:
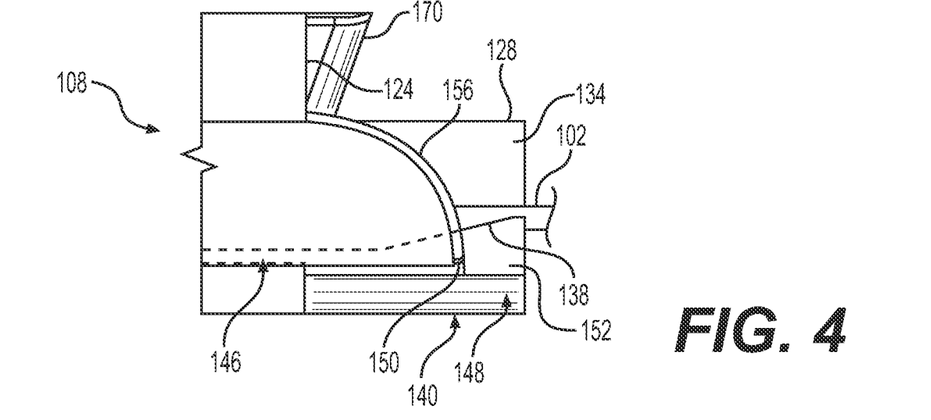
FIG. 4 shows a side view of the tip of the endoscope of FIG. 1 in a first configuration, in accordance with aspects of the present disclosure.
Figure 5:
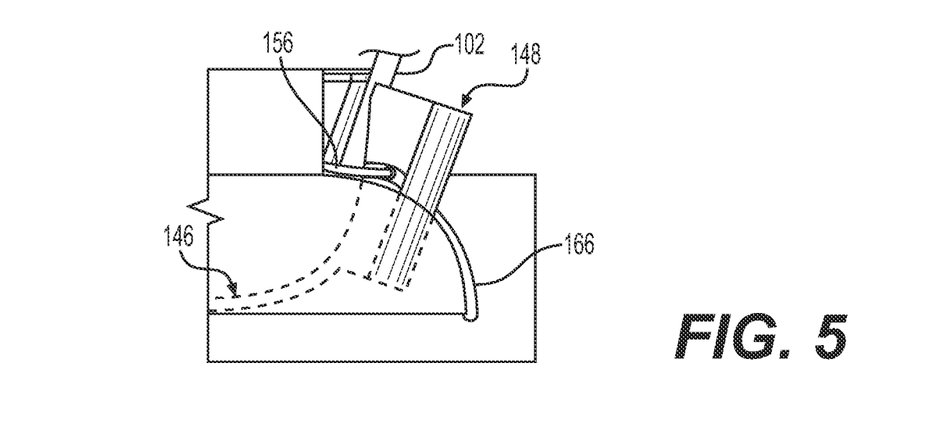
FIG. 5 shows a side view of the tip of the endoscope of FIG. 1 in a second configuration, in accordance with aspects of the present disclosure.

By pulling one or both of first portion 156 and second portion 158 of control wire 122 in a proximal direction, the user may retract control wire 122 into control wire openings 110 and 112. This retraction may cause proximal portion 146 of elevator 140 to bend as distal portion 148 of elevator 140 is drawn toward distal-facing surface 124. FIGS. 3 and 4 show views of tip 108 where elevator 140 is at rest, while FIG. 5 shows a view of tip 108 where proximal portion 146 of elevator 140 is bent due to forces exerted on distal portion 148 of elevator 140 by control wire 122. Pulling both of first portion 156 and second portion 158, which are on opposite sides of elevator 140, may ensure that elevator 140 may be drawn toward distal-facing surface 124 with little or no twisting or torqueing, to ensure that instrument 102 is brought into a desired position.

Instrument 102 may be held in indentation 168 of distal portion 148 as distal portion 148 is drawn toward distal-facing surface 124. As distal portion 148 is deflected, distal portion 148 may deflect instrument 102, thereby adjusting the position of instrument 102. Instrument 102 may be extended out of, retracted into, and/or rotated (e.g., twisted) in the working lumen of shaft 104 and working opening 114 before, during, and/or after instrument 102 is deflected by distal portion 148. Continued pulling of control wire 122 may cause distal portion 148 to pin instrument 102 against a protrusion 170 on distal-facing surface 124. This may lock instrument 102 in place relative to tip 108. When locked, the ability to extend, retract, and/or rotate instrument 102 may be hindered or eliminated. In one example, protrusion 170 may have a shape complementary to a shape of indentation 168 to facilitate holding or locking of instrument 102 between protrusion 170 and distal portion 148. For example, protrusion 170 may have a wedge-like shape. When the user ceases to pull control wire 122, and/or extends control wire 122 distally, proximal portion 146 may inherently seek to move to its unbent state, thereby moving distal portion 148 away from distal-facing surface 124 and back toward its orientation as shown in FIGS. 2-4. This may unlock instrument 102.

Device 100 also may include a handle 172 coupled to a proximal end of shaft 104. Handle 172 may include one or more lumens (not shown) that communicate with the lumen(s) of shaft 104. Handle 172 also may include one or more ports 174 that open into the one or more lumens of handle 172. For example, instrument 102 may be inserted into port 174 on its way to the working lumen of shaft 104. In one example, handle 172 may include a cable 176. Cable 176 may couple one or more external systems (not shown) to device 100. Cable 176 may, for example, couple handle 172 to a fluid supply, an illumination source, and/or an imaging processor or display.

Handle 172 also may include an actuation mechanism 178. Actuation mechanism 178 may include one or more knobs, buttons, levers, switches, and/or any other suitable actuators, for controlling at least one of deflection of shaft 104, the delivery of fluid, the emission of illumination, and/or imaging functions. In one example, actuation mechanism 178 may be operatively coupled to proximal portions (not shown) of control wire 122 that extend proximally from control wire openings 110 and 112 into handle 172. The user may manipulate actuation mechanism 178 to selectively exert at least one of a pulling force and a pushing force on control wire 122 to control the position of elevator 140, and thereby control the position of instrument 102.

Figure 6:
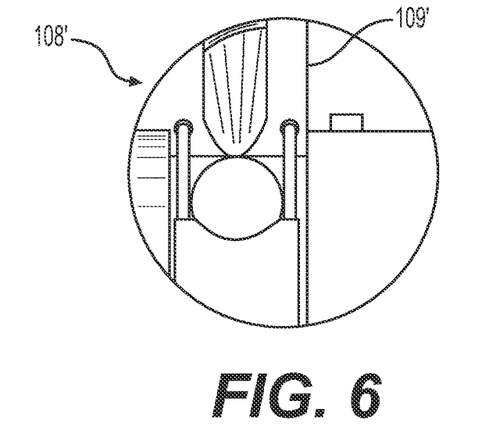
FIG. 6 shows a front view of an alternative endoscope tip, in accordance with aspects of the present disclosure.

FIG. 6 shows an alternative embodiment of a tip 108'. Tip 108' may be similar to tip 108, except tip 108' may be made of separate components coupled together at a joint 109'. In one example, portions of tip 108' on a first side of joint 109' may be a single, monolithic component, while portions of tip 108' on a second side of joint 109' may be another single, monolithic component. By producing the components separately and then joining them together, one material may be used for one of the components, while another material (with different properties) may be used for the other component. For example, the component to the left of joint 109' may be made of a material that is more flexible than the material used to make the component to the right of joint 109', to facilitate bending of the elevator.

In the example shown in FIG. 6, the component to the left of joint 109' may include an elevator, a working opening, control wire openings, a distal-facing surface, a lateral-facing sidewall, and/or a posterior-facing surface, similar to those of tip 108. The component to the right of joint 109' may include a fluid opening, a lateral-facing sidewall, an anterior-facing surface, an imaging opening, and/or an illumination opening, similar to those of tip 108. It should be understood, however, that joint 109' may divide tip 108' in any other suitable manner. It also is contemplated that joint 109' may follow a straight line across tip 108', or may include one or more bends and/or corners, as it crosses tip 108'. It also is contemplated that joint 109' may divide tip 108' into more than two components.

Figure 7A:
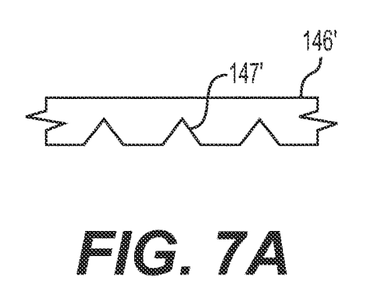
FIGS. 7A and 7B show top and side views of a living hinge of an endoscope tip, in accordance with aspects of the present disclosure.
Figure 7B:
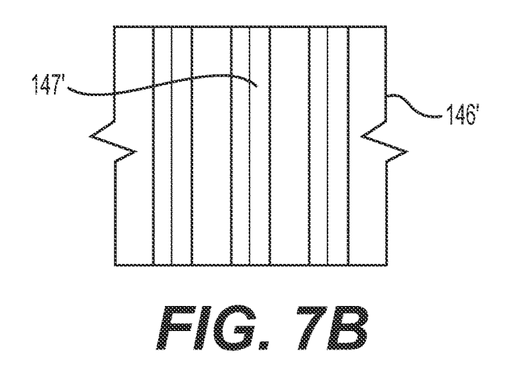

FIGS. 7A and 7B show views of an alternative embodiment of a proximal portion 146' of an elevator. Proximal portion 146' may have one or more elements thereon for precisely controlling bending of proximal portion 146'. In one example, proximal portion 146' may include cutouts or indentations 147' (e.g., notches, grooves, slots, holes, and the like) to facilitate bending by creating thinner portions of proximal portion 146'. Additionally or alternatively, proximal portion 146' may include protrusions (e.g., ridges, spines, and the like) (not shown) to limit bending by creating thicker portions of proximal portion 146'. The cutouts, indentations, and/or protrusions may be on a posterior-facing surface of proximal portion 146', an anterior-facing surface of proximal portion 146', and/or one or more lateral-facing surfaces of proximal portion 146'.

Figure 8A:
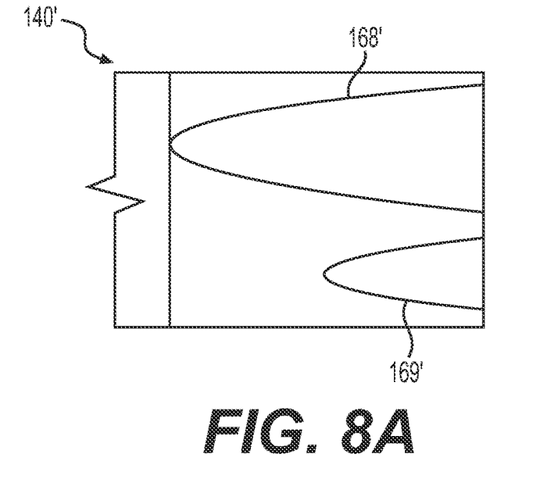
FIGS. 8A and 8B show top and front views of an elevator, in accordance with aspects of the present disclosure.
Figure 8B:
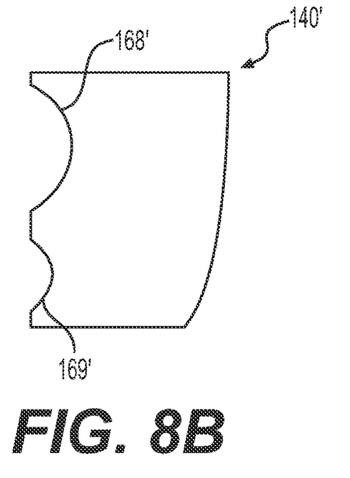

FIGS. 8A and 8B show views of an alternative embodiment of an elevator 140' including a plurality of indentations 168' and 169'. Indentations 168' and 169' may have different characteristics. For example, one of indentations 168' and 169' may be wider, deeper, and/or longer than the other. Indentation 168' may be sized to hold larger instruments, and indentation 169' may be sized to hold smaller instruments.

It will be apparent to those skilled in the art that various modifications and variations can be made in the disclosed systems and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A device, comprising:
a shaft;
a distal tip including an interior sidewall and a first channel positioned on the interior sidewall; and
an elevator including an exterior sidewall, a proximal portion that is fixed relative to the interior sidewall, a distal portion that is movable relative to the proximal portion, and a second channel positioned on the exterior sidewall;
wherein, when the elevator moves to a first position, the first channel and the second channel are each configured to receive a portion of a control wire, and when the elevator moves to a second position the control wire is configured to move out of the first channel and remain inside the second channel;
wherein the proximal portion bends relative to the distal portion when the elevator moves from the first position to the second position,
wherein the distal tip includes a distally-facing surface defining a first control wire opening and a second control wire opening, wherein a first portion of the control wire extends from the first control wire opening, wherein a second portion of the control wire extends from the second control wire opening, and wherein a third portion of the control wire extends between the first portion and the second portion at the distal portion of the elevator.

2. The device of claim 1, wherein the shaft is configured to receive an instrument that extends distally out of the distal tip, and the elevator is configured to deflect the instrument relative to the distal tip when moving from the first position to the second position, thereby causing the control wire to move out of the first channel.

3. The device of claim 1, wherein the distal portion of the elevator includes a width defined between the exterior sidewall and an opposing exterior sidewall of the elevator.

4. The device of claim 3, wherein the elevator includes an opening positioned within the second channel and a passage that extends across the width of the distal portion and terminates at the opening.

5. The device of claim 4, wherein the elevator includes a second opening positioned on an opposing exterior sidewall that is opposite of the exterior sidewall of the elevator, and the passage terminates at the second opening.

6. The device of claim 5, wherein the control wire received within the second channel enters the passage at the opening and exits the passage at the second opening.

7. The device of claim 4, wherein the passage has a length that is less than the width of the distal portion.

8. A device, comprising:
a shaft;
a distal tip including an interior surface and a first channel extending along the interior surface; and an elevator including an exterior surface, a proximal portion that is fixed relative to the interior surface of the distal tip, a distal portion that is movable relative to the proximal portion, and a second channel extending along the exterior surface;

wherein, when the elevator moves to a lowered position, the first channel is configured to receive a proximal portion of a control wire and the second channel is configured to receive a distal portion of the control wire, and when the elevator moves to a raised position the proximal portion of the control wire is guided out of the first channel and the distal portion of the control wire is retained inside the second channel, wherein the proximal portion bends relative to the distal portion when the elevator moves from the lowered position to the raised position, wherein the distal tip includes a distally-facing surface defining a first control wire opening and a second control wire opening, wherein a first portion of the control wire extends from the first control wire opening, wherein a second portion of the control wire extends from the second control wire opening, and wherein a third portion of the control wire extends between the first portion and the second portion at the distal portion of the elevator.

9. The device of claim 8, wherein the first channel is at least partially open along the interior surface of the distal tip for receiving the proximal portion of the control wire, and the second channel is at least partially open to the exterior surface of the elevator for receiving the distal portion of the control wire.

10. The device of claim 8, wherein the control wire is configured to move the elevator to the raised position in response to the proximal portion moving proximally relative to the distal tip, such that an instrument received on the elevator is deflected relative to the distal tip.

11. The device of claim 8, wherein the control wire is configured to move the elevator to the lowered position in response to the proximal portion moving distally relative to the distal tip, such that an instrument received on the elevator is longitudinally aligned with the distal tip.

12. The device of claim 8, wherein the proximal portion of the control wire exits the first channel when the elevator moves from the lowered position to the raised position, and wherein the proximal portion of the control wire enters the first channel when the elevator moves from the raised position to the lowered position.

13. The device of claim 8, wherein the distal portion of the elevator includes an indentation, wherein the distally-facing surface of the distal tip includes a protrusion that is complementary to the indentation of the elevator, and wherein the protrusion is configured to face the distal portion of the elevator when in the raised position.

14. The device of claim 8, wherein the distal portion of the control wire remains fixed relative to the second channel when the elevator moves between the lowered position and the raised position.

15. A device, comprising:
a shaft;
a distal tip including an interior surface and a first channel on the interior surface; and
an elevator including an outer surface, a proximal portion that is fixed relative to the interior surface, a distal portion that is movable relative to the proximal portion, and a second channel on the outer surface;
wherein, when the elevator is undeflected relative to the distal tip, each of the first channel and the second channel are configured to receive a control wire, and when the elevator is deflected relative to the distal tip, the first channel is configured to release the control wire and the second channel is configured to hold the control wire;
wherein the proximal portion bends relative to the distal portion when the elevator deflects relative to the distal tip, and
wherein the distal tip includes a distally-facing surface defining a first control wire opening and a second control wire opening, wherein a first portion of the control wire extends from the first control wire opening, wherein a second portion of the control wire extends from the second control wire opening, and wherein a third portion of the control wire extends between the first portion and the second portion at the distal portion of the elevator.

16. The device of claim 15, wherein the control wire moves out of the first channel when the control wire translates proximally relative to the shaft to deflect the elevator proximally relative to the distal tip, such that the control wire is removed from the first channel, and wherein the control wire remains inside the second channel when the control wire translates proximally relative to the shaft to deflect the elevator proximally relative to the distal tip, such that the control wire moves with the elevator.

17. The device of claim 15, wherein the distal portion of the elevator includes an indentation configured to receive a portion of an instrument therein, and wherein the distally-facing surface of the distal tip includes a protrusion that is complementary to the indentation of the elevator, wherein the protrusion is configured to face the distal portion of the elevator when deflected relative to the distal tip.

18. The device of claim 17, wherein the protrusion is positioned between the first control wire opening and the second control wire opening.

19. The device of claim 15, wherein the first portion, the second portion, and the third portion of the control wire form a U-shape.

20. The device of claim 15, wherein the elevator includes a third channel on a second exterior sidewall of the elevator, the first portion of the control wire extends from the first control wire opening to the second channel, and the second portion of the control wire extends from the second control wire opening to the third channel.

* * * * *